(12) United States Patent
Bredif et al.

(10) Patent No.: US 9,846,224 B2
(45) Date of Patent: Dec. 19, 2017

(54) ULTRASOUND IMAGING METHOD AND DEVICE WITH PREDICTION OF ARTEFACTS INDUCED BETWEEN RECONSTRUCTION MODES

(71) Applicant: COMMISSARIAT A L'ENERGIE ATOMIQUE ET AUX ENE ALT, Paris (FR)

(72) Inventors: Philippe Bredif, Paris (FR); Ekaterina Iakovleva, Limours (FR); Sylvain Chatillon, Palaiseau (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 751 days.

(21) Appl. No.: 14/332,821

(22) Filed: Jul. 16, 2014

(65) Prior Publication Data

US 2015/0023136 A1   Jan. 22, 2015

(30) Foreign Application Priority Data

Jul. 17, 2013   (FR) ..................................... 13 57036

(51) Int. Cl.
*G01S 7/00* (2006.01)
*G01S 7/52* (2006.01)
(Continued)

(52) U.S. Cl.
CPC ........ *G01S 7/52017* (2013.01); *G01N 29/069* (2013.01); *G01N 29/0672* (2013.01);
(Continued)

(58) Field of Classification Search
USPC .......................................................... 367/11
See application file for complete search history.

(56) References Cited

U.S. PATENT DOCUMENTS 6,322,507 B1 * 11/2001 Passi .................... A61B 8/0875
                                                                600/437
6,585,763 B1 *  7/2003 Keilman .............. A61B 5/0031
                                                                604/891.1
(Continued)

OTHER PUBLICATIONS

French Preliminary Search Report dated May 16, 2014 in French Application 13 57036, filed on Jul. 17, 2013 ( with English Translation of Categories of Cited Documents).
(Continued)

*Primary Examiner* — James R Hulka
(74) *Attorney, Agent, or Firm* — Oblon, McClelland, Maier & Neustadt, L.L.P.

(57) ABSTRACT

The invention relates to an ultrasound imaging method for imaging a part (1), characterized by the implementation of the following steps:
 selecting a first sub-region ($\tilde{Z}$) of the part from a first image ($I^A(Z)$) of a region (Z) of the part (1),
 determining, for each point of the first selected sub-region ($\tilde{Z}$), the times of flight ($T_{ij}^A(\tilde{Z})$) corresponding to the paths according to a first reconstruction mode (A) going through the point from a transmitter i to a receiver j for a set of M*N transmitter-receiver couples of an ultrasound signal;
 determining a second sub-region of the part, a point (P) of the region belonging to the second sub-region when a time of flight ($T_{ij}^B(P)$) of the path according to a second reconstruction mode (B) going through the point (P) from a transmitter i to a receiver j of said set of M*N transmitter-receiver couples coincides with a time of flight ($T^A(\tilde{Z})$) of a path according to the first reconstruction mode from a transmitter to a receiver from the transmitter i to the receiver j going through one of the points of the first selected sub-region.

8 Claims, 8 Drawing Sheets

(51) Int. Cl.
*G01N 29/06* (2006.01)
*G01N 29/07* (2006.01)
*G01N 29/26* (2006.01)
*G10K 11/34* (2006.01)

(52) U.S. Cl.
CPC ........... *G01N 29/07* (2013.01); *G01N 29/262* (2013.01); *G01S 7/52046* (2013.01); *G10K 11/346* (2013.01)

(56) References Cited

U.S. PATENT DOCUMENTS

| | | | |
|---|---|---|---|
| 6,623,430 B1* | 9/2003 | Slayton | A61B 5/01 600/439 |
| 2002/0026118 A1* | 2/2002 | Govari | A61B 5/0422 600/462 |
| 2002/0151767 A1* | 10/2002 | Sonnenschein | A61B 1/0005 600/117 |
| 2003/0013958 A1* | 1/2003 | Govari | A61B 5/0422 600/437 |
| 2003/0018244 A1* | 1/2003 | Haddad | A61B 5/05 600/371 |
| 2004/0127791 A1* | 7/2004 | Mast | A61B 5/015 600/438 |
| 2005/0187488 A1* | 8/2005 | Wolf | A61B 5/0017 600/561 |
| 2005/0228597 A1* | 10/2005 | Giurgiutiu | G01M 5/0033 702/35 |
| 2012/0001875 A1* | 1/2012 | Li | G01S 7/5273 345/177 |

OTHER PUBLICATIONS

S. Robert et al. "Methodes Ultrasonores De Detection Et D'Imagerie Temps-Reel Implementees Dans Les Systemes D'Acquisition M2M", Journees Cofrend "Conferences Et Exposition Sur Les Essais Non Destructifs", XP-55037304, 2011, 13 pages.

Severine Paillard et al. "New Ultrasonic Array Imaging of Crack-Type Defects Based on Simulation-Helped Processing", 10$^{th}$ European Convention on Non-Destructive Testing, XP-002724437, 2010, 8 pages.

J. Zhang et al. "The Use of Scattering Matrix to Model Multi-Modal Array Inspection With the TFM", Review of Progress in Quantiproceedings of the 35$^{th}$ Annual Review of Progress in Quantitative Nondestructive Evaluation. AIP Conference Proceedings, vol. 1096, XP-002724438, 2009, 8 pages.

Ekaterina Iakovleva et al. "Multi-Mode TFM Imaging with Artifacts Filtering using CIVA UT Forwards Models", AIP Conference Proceedings, vol. 1581, XP-002724439, 2014, 8 pages.

* cited by examiner

ULTRASOUND IMAGING METHOD AND DEVICE WITH PREDICTION OF ARTEFACTS INDUCED BETWEEN RECONSTRUCTION MODES

TECHNICAL FIELD

The field of the invention is that of ultrasound imaging. The invention applies in particular to the non-destructive testing of industrial parts or installations for detecting therein the presence of potential defects, localising them and dimensioning them. The invention more particularly relates to an ultrasound imaging method using a multiple element transducer and based on synthetic focusing techniques.

STATE OF THE PRIOR ART

In the field of non-destructive testing using ultrasounds, one of the most developed methods of synthetic focusing, known as the "total focusing reconstruction method" (TFM) consists in a synthetic focusing of the fields transmitted and received by coherent summation of the data derived from an acquisition of the Full Matrix Capture (FMC) or inter-element matrix type.

The FMC acquisition method consists in transmitting successively via M ultrasound transmitters an ultrasound wave in the part to be imaged, and recording in N ultrasound receivers the echoes coming from the propagation of the waves transmitted in the part. The method then results in the formation of M*N elementary signals $S_{ij}(t)$ with $1 \leq i \leq M$ and $1 \leq j \leq N$.

The TFM reconstruction method consists in summating in a coherent manner the elementary signals so as to obtain amplitude maxima, corresponding to constructive interferences, for the points of the part where are effectively localised defects generating echoes of the ultrasound waves transmitted. The coherence of the signals is determined from the durations of the theoretical paths of the ultrasound waves propagating in the part between a given transmitter and a receiver and going through the considered point.

The TFM reconstruction method comprises the following steps:
- defining a reconstruction area (positions, dimensions and number of calculation points);
- for each point P of the reconstruction area, and for each transmitter-receiver ij couple, calculating the theoretical time of flight, $T_{ij}(P)$ corresponding to the path between the transmitter i and the receiver j going through the point P;
- for each point P of the area, summation of the amplitudes extracted from the signals $S_{ij}(t)$ at the times $t=T_{ij}(P)$, which may be written $$I(P) = \sum_{i=1}^{M} \sum_{j=1}^{N} S_{ij}(T_{ij}(P)).$$

The focusing may be carried out by considering several reconstruction modes which are characterised by different types of route (direct, corner echoes, indirect echoes, etc.) and several modes of propagation of the waves (longitudinal or transversal).

Figure 1A:
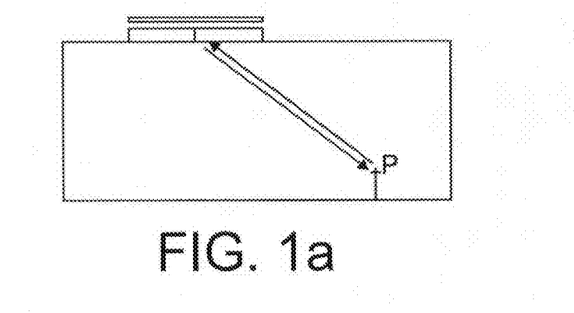
FIG. 1a is an illustration of a direct time of flight route.

For a direct type route, the paths taken into account for the calculation of the times of flight correspond to direct routes between the different elements of the sensor and the points of the reconstruction area, in other words without rebound on the bottom of the part, as illustrated in FIG. 1a.

Figure 1B:
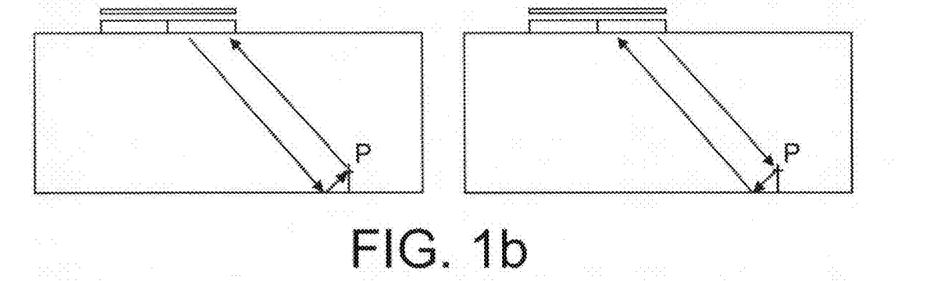
FIG. 1b is an illustration of an indirect echo-type time of flight route.
Figure 1C:
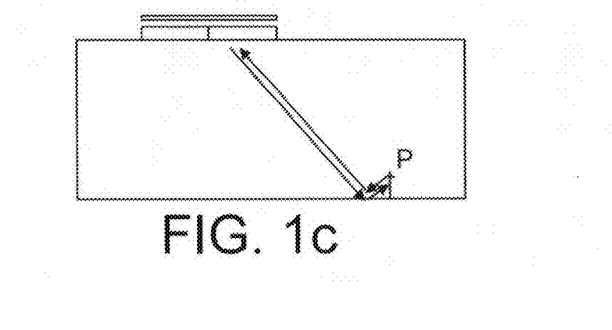
FIG. 1c is another illustration of an indirect echo-type time of flight route.

For routes of corner echo and indirect echo type, and as illustrated by FIGS. 1b and 1c, the routes taken into account for the calculation of the times of flight include one or more reflections on the bottom in the course of the route between the transmitter and the point of the reconstruction area and/or in the course of the route between the point of reconstruction and the receiver. More precisely, the corner echo mode takes into consideration a reflection of the ultrasound wave on the bottom of the part, before or after an interaction with the point to be reconstructed, whereas the indirect echo mode takes into account both a reflection before the interaction with the point to be reconstructed and a reflection after.

TFM focusing in corner echo mode and that in indirect mode typically make it possible to complete the information items supplied by TFM focusing in direct mode, because they exploit contributions involving other physical phenomena and deriving from interactions with different portions of the part and the defect. They make it possible in particular to image other portions of the defect. For example, in certain cases, the reconstruction in corner echo mode has the advantage of imaging a defect of the part over its whole length, and not uniquely its ends.

Apart from the type of route, a reconstruction mode is also characterised by the mode of propagation of the ultrasound signal (longitudinal, transversal) on each portion of the route. The letters L and T are conventionally used to designate respectively a longitudinal, respectively transversal propagation. In the case of direct routes, the first letter corresponds to the route between the transmission and the place of reconstruction in the part, the second to the route between said place and the reception. In the case of corner echo routes, the first letter represents the route between the transmission and the bottom of the part, the second the route between the bottom of the part and the place of reconstruction, the third the route between said place and the reception.

Figure 2A:
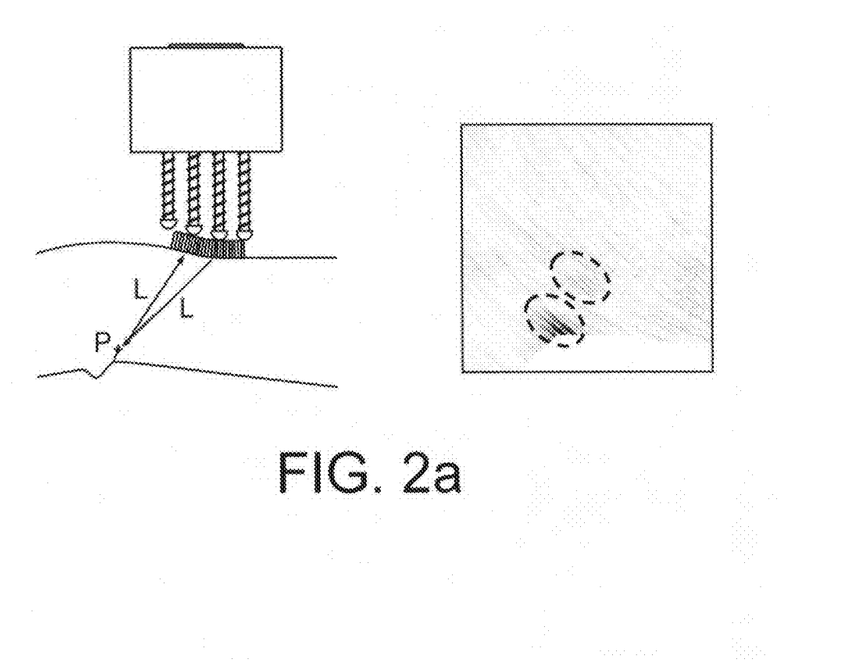
FIG. 2a is an illustration of reconstruction results by TFM from experimental data.
Figure 2B:
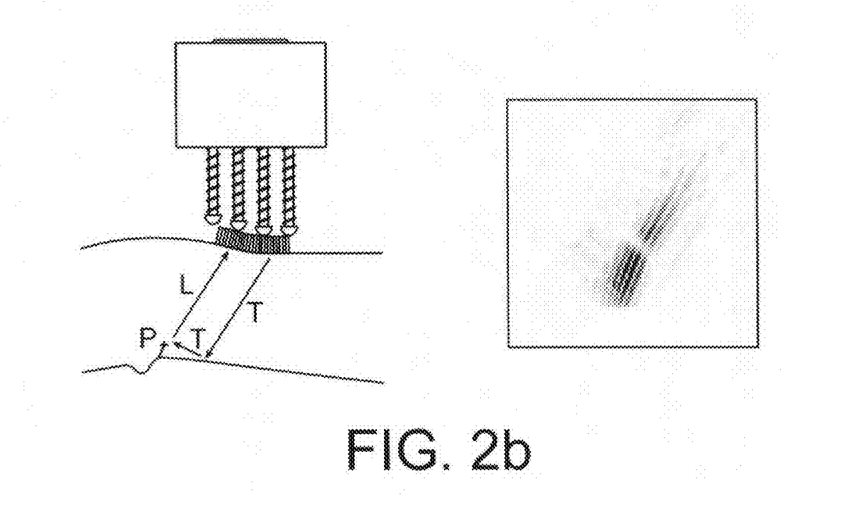
FIG. 2b is another illustration of reconstruction results by TFM from experimental data.

An example of result of reconstruction by TFM from experimental data is shown in FIGS. 2a and 2b. This result shows that the combined exploitation of different reconstruction modes has an interest for the characterisation of defects. In fact, in the case of a reconstruction according to the direct LL mode, the two diffraction echoes (surrounded by dotted lines in the image on the right of FIG. 2a) are correctly repositioned at the two ends, upper and lower, of the cut, whereas for a reconstruction in TTL corner echo mode, the latter is correctly repositioned over the whole length of the cut (cf. image on the right of FIG. 2b). The two diffraction echoes then make it possible to determine the height of the defect and the corner echo makes it possible to determine its orientation.

However, multi-mode TFM reconstructions carried out on different geometries have highlighted the presence of indications having no physical origin in the inspected component. The analysis of such indications, also known as reconstruction artefacts, shows that their presence is due to equivalent path times for different reconstruction modes. Echoes of defects or geometry detected by certain modes may be reconstructed for other modes from the moment there is coincidence of the times of flight.

Figure 3A:
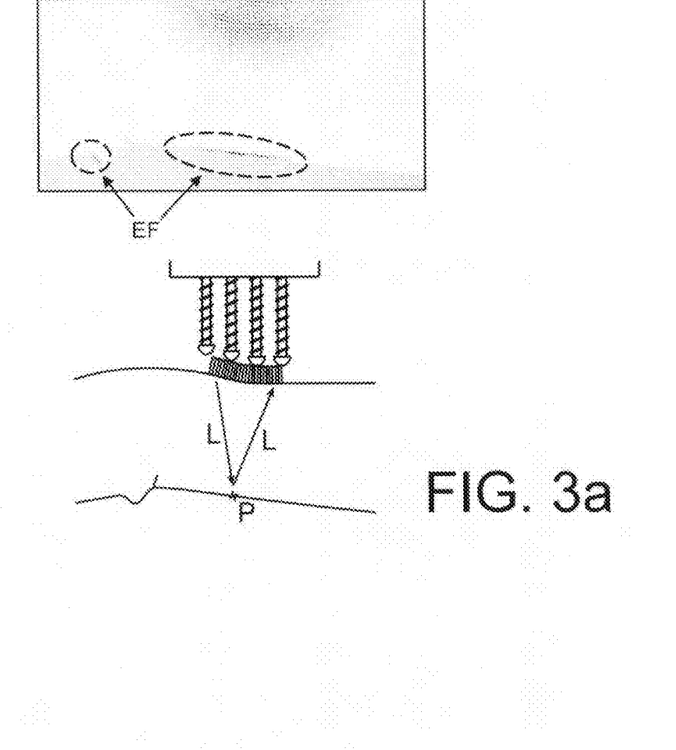
FIG. 3a is an illustration of an artefact from a geometry echo.
Figure 3B:
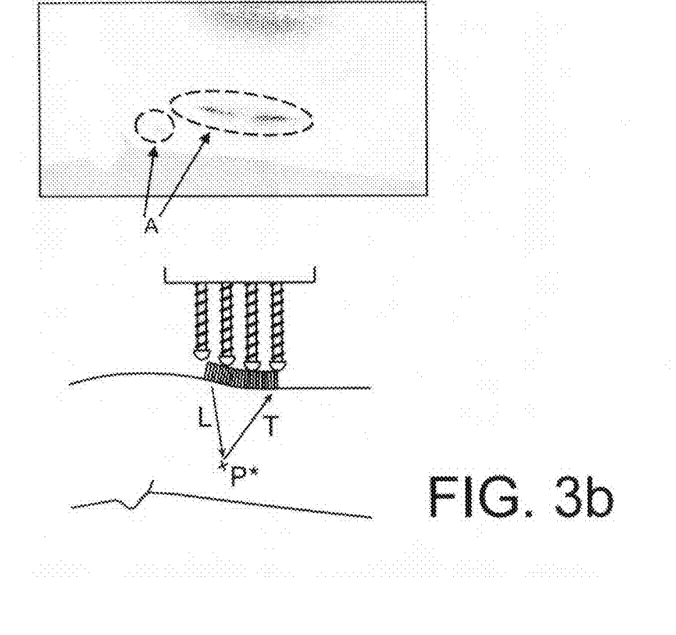
FIG. 3b is another illustration of an artefact from a geometry echo.

An example of this type of artefact coming from the geometry echo is presented in FIGS. 3a-3b. This example illustrates the fact that an indication actually detected in a reconstruction in direct LL mode generates a contribution in the reconstruction in direct LT mode in the areas where the times of flight coincide. For the reconstruction obtained in LL mode (FIG. 3a), the geometry echo EF, corresponding to the reflection of the ultrasound wave on the bottom of the part, is correctly repositioned in the part. For the reconstruction in LT mode (FIG. 3b), the presence of artefacts A of very strong amplitude may be noted underneath the geometric aperture of the sensor. These reconstruction artefacts stem from the fact that, for a transmitter-receiver couple, for a point of reconstruction P* according to the LT mode, the corresponding time of flight is identical to that of point P (still for the same transmitter-receiver couple) reconstructed at a different position in the part according to the LL mode. It ensures that the amplitude attributed to the point P during LL reconstruction is attributed to the point P* during LT reconstruction. In this example, if the amplitude of P is linked to the echo coming from the bottom of the part, this will be attributed in an inappropriate manner to the point P* thereby inducing the appearance of an artefact in LT mode.

As this example shows, the risk of confusion between an indication associated with a defect and a reconstruction artefact is not negligible. Nevertheless, if the presence of artefacts in reconstructions obtained by synthetic focusing techniques or conventional focusing techniques is a well-known fact, at the present time, the procedures for the identification of such artefacts are complex and are based on knowledge of the geometry of the part and the defect. They are moreover limited to the identification of artefacts coming from the geometry echo.

There thus exists a need for tools that make it possible to analyse the artefacts present in reconstructions by multi-mode synthetic focusing, while making it possible to distinguish in particular echoes due to defects from those due to the geometry of the part, and to filter the undesirable echoes, while remaining simple to implement.

DESCRIPTION OF THE INVENTION

The invention aims to meet these needs and to do so proposes, according to a first aspect, an ultrasound imaging method for imaging a part, characterised by the implementation of the following steps implemented by a processor coupled to a set of M*N transmitter-receiver couples of an ultrasound signal:
  selecting a first sub-region of the part from a first image of a region of the part;
  determining, for each point of the first selected sub-region, times of flight corresponding to the path according to a first reconstruction mode going through the point from a transmitter i to a receiver j for the set of M*N transmitter-receiver couples of an ultrasound signal;
  determining a second sub-region of the part, a point of the region belonging to the second sub-region when a time of flight of the paths according to a second reconstruction mode going through the point from a transmitter i to a receiver j of said set of M*N transmitter-receiver couples coincides with a time of flight of a path according to the first reconstruction mode from the transmitter i to the receiver j going through one of the points of the first selected sub-region.

Certain preferred but non-limiting aspects of this method are the following:
  it comprises a reconstruction of a second image of the region of the part by a synthetic focusing according to the second reconstruction mode according to which, for each point of the region, and for each transmitter-receiver i-j couple, an ultrasound signal considered at a time of flight of the path according to the second reconstruction mode from the transmitter i to the receiver j while going through the point of the region is exploited, uniquely if said time of flight according to the second reconstruction mode coincides with a time of flight of a path according to the first reconstruction mode from the transmitter i to the receiver j going through one of the points of the first selected sub-region;
  it comprises a reconstruction of a second image of the region of the part by a synthetic focusing according to the second reconstruction mode according to which, for each point of the region, and for each transmitter-receiver i-j couple, an ultrasound signal considered at a time of flight of the path according to the second reconstruction mode from the transmitter i to the receiver j while going through the point of the region is exploited, uniquely if said time of flight according to the second reconstruction mode differs from the times of flight of the paths according to the first reconstruction mode from the transmitter i to the receiver j going through the points of the first selected sub-region.
  a reconstruction mode is characterised by a type of route comprising several portions and a mode of propagation of the ultrasound signal on each portion of the route;
  the first reconstruction mode is a mode according to which each ultrasound signal follows a direct route with two portions, the mode of propagation of the signal being lateral on each of the portions;
  the second reconstruction mode is a mode according to which each ultrasound signal follows a direct route with two portions and the mode of propagation of the signal is different on each of the portions, or a mode according to which each ultrasound signal follows an indirect route with three portions at least.

BRIEF DESCRIPTION OF THE DRAWINGS

Other aspects, aims, advantages and characteristics of the invention will become clearer from reading the following detailed description of preferred embodiments thereof, given as non-limiting examples, and made with reference to the appended drawings in which.

DETAILED DESCRIPTION OF PARTICULAR EMBODIMENTS

The invention relates to an ultrasound imaging method for imaging a part, implementing a reconstruction by synthetic focusing, for example total focusing, by means of a processor coupled to a multiple element transducer 1.

Figure 4A:
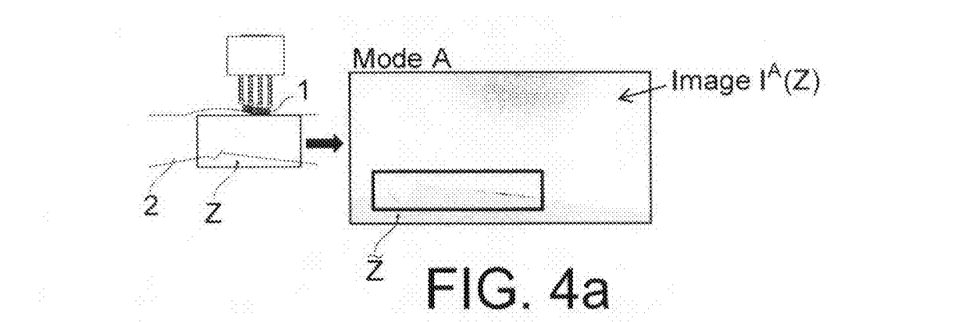
FIG. 4a illustrates and a first reconstruction mode of direct LL type.

With reference to FIG. 4a, the method exploits the multiple element transducer 1 arranged on the surface of a part 2 to be imaged, comprising M transmitters of an ultrasound signal, indexed i, and N receivers of an ultrasound signal, indexed j, supplying signals $S_{ij}(t)$ representative of the echo of the ultrasound wave received for a transmission by a transmitter i and a reception by a receiver j.

Still with reference to FIG. 4a, the method comprises a first step of selecting a first sub-region $\tilde{Z}$ of the part 2 from a first image $I^A(Z)$ of a region Z ($\tilde{Z} \subset Z$) of the part 2.

This selection may be performed manually by an operator who visualises and selects a sub-region that contains an echo, the origin of which is identifiable (echo of the bottom of the part, or defect echo for example). In a variant, the selection of the sub-region may be automated, for example using automatic image analysis tools able to plot the contours of sub-regions having the largest amplitudes (typically by thresholding of the image and conservation of the points for which the amplitudes are above the threshold).

The method then comprises a step of determining, for each point P of the first selected sub-region $\tilde{Z}$, times of flight of the paths according to a first reconstruction mode going through the point P from a transmitter i to a receiver j for the set of M*N transmitter-receiver couples. In other words, the times of flight are extracted according to the first reconstruction mode associated with each point of the selected sub-region for a given reconstruction mode. One then forms, for each of the M*N transmitter-receiver couples, a sub-set of times of flight $T_{ij}^A(\tilde{Z})$ comprising the set of times of flight according to the first reconstruction mode (A mode) from the transmitter i to a receiver j going through one of the points of the selected sub-region $\tilde{Z}$.

In a possible embodiment of the invention, the method comprises a step of reconstructing said first image $I^A(Z)$ of the region Z by a synthetic focusing according to the first reconstruction mode of ultrasound waves (A mode) exploiting, for each point P of the region, the M*N ultrasound signals $S_{ij}(t)$ considered, for each transmitter-receiver i-j couple, at a time of flight $T_{ij}^A(P)$ corresponding to the path according to said first reconstruction mode from the transmitter i to the receiver j while going through the point P of the region. The set of these times of flight, calculated for all the transmitter-receiver i-j couples and for all the points P of the reconstructed region Z, is denoted $T^A(Z) = \{T_{ij}^A(Z)\}_{i=1,\ldots,M, j=1,\ldots,N}$. Within the scope of this embodiment, the different sub-sets of times of flight $T_{ij}^A(\tilde{Z})$ are then known from the reconstruction of the first image according to the first A mode.

The method further comprises a step of determining a second sub-region of the part, a point P of the region Z belonging to the second sub-region when a time of flight $T_{ij}^B(P)$ of the path according to a second reconstruction mode (B mode) going through the point P from a transmitter i to a receiver j of said set of M*N transmitter-receiver couples coincides with a time of flight of a path according to the first reconstruction mode going through one of the points of the first selected sub-region from the transmitter i to the receiver j ($T_{ij}^B(P) \in T_{ij}^A(\tilde{Z})$).

Figure 4B:
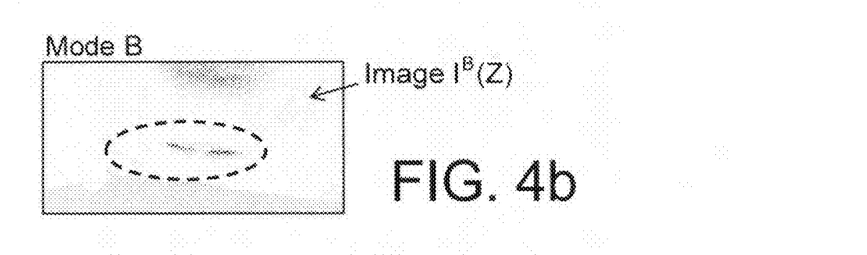
FIG. 4b is an illustration of a second reconstruction mode of direct LT type.

As an example, the echoes present in the selected sub-region $\tilde{Z}$ of FIG. 4a induce artefacts in an image reconstructed according to the B mode in the area surrounded by dotted lines in FIG. 4b which comprises the points for which the time of flight in B mode corresponds to a time of flight in A mode going through a point of the selected sub-region Ž. It will thus be understood that the invention performs a transformation in B mode of the selected sub-region Ž.

In a possible embodiment of the invention, the method further comprises a step of reconstruction of a second image $I^B(Z)$ of the region Z of the part by a synthetic focusing according to the second reconstruction mode (B mode). But unlike a conventional reconstruction exploiting the set of times of flight for all the transmitter-receiver couples and all the points of the region, the reconstruction of the second image according to the invention implements an isolation, or a contrario a filtering, of reconstruction artefacts.

The method may thus comprise a reconstruction of a second image $I^B(Z)$ of the region Z of the part according to the second reconstruction mode (B mode) exploiting, for each point P of the region Z, and for each transmitter-receiver i-j couple, an ultrasound signal $S_{ij}(t)$ considered at a time of flight $T_{ij}^B(P)$ of the path according to the second reconstruction mode from the transmitter i to the receiver j while going through the point P of the region, uniquely if said time of flight $T_{ij}^B(P)$ coincides with (isolation of artefacts), respectively differs from (filtering of artefacts), a time of flight of a path according to the first reconstruction mode going through one of the points of the selected sub-region from the transmitter i to the receiver j.

In other words, the reconstruction of the second image according to the B mode exploits, during an isolation of artefacts, and for a given transmitter-receiver i-j couple, uniquely the times of flight extracted beforehand forming the sub-set $T_{ij}^A(\tilde{Z})$. A contrario, the reconstruction of the second image according to the B mode exploits, during a filtering of artefacts, and for a given transmitter-receiver i-j couple, uniquely the times of flight not belonging to the sub-set extracted beforehand $T_{ij}^A(\tilde{Z})$.

Figure 6A:
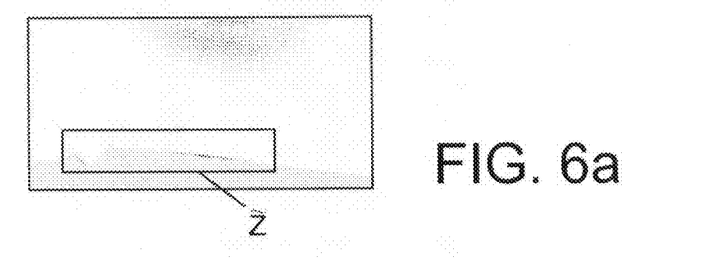
FIG. 6a illustrates the application of a method according to the invention with a first reconstruction mode of direct LL type and a second reconstruction mode of direct LT type.
Figure 6B:
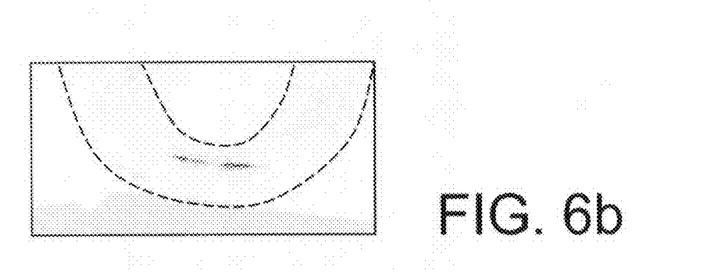
FIG. 6b is another illustration of the application of a method according to the invention with a first reconstruction mode of direct LL type and a second reconstruction mode of direct LT type.

In the case of an isolation, the indications present in the selected sub-region Ž from the first image $I^A(Z)$ have the same origin as those present in the reconstruction of the second image. In the example of FIGS. 6a and 6b, it is then possible to deduce that the indications linked to the echo from the bottom of the part and to the detected defect echo (zone Ž) according to the first A mode induces the artefacts surrounded by dotted lines in the second image $I^B(Z)$.

To carry out the isolation of reconstruction artefacts in the second image, one determines, for each point P of the region Z, a sum of amplitudes of the acoustic signals only taking account of the acoustic signals received at a receiver j from a transmitter i when the time of flight $T_{ij}^B(P)$ of the path according to the second reconstruction mode from the transmitter i to the receiver j while going through the point P coincides with a time of flight of a path according to the first reconstruction mode from the transmitter i to the receiver j while going through one of the points of the selected sub-region $(T_{ij}^B(P) \in T_{ij}^A(\tilde{Z}))$.

Thus, during the reconstruction according to the B mode, the contributions $S_{ij}(T_{ij}^B(P))$ of the points for which the times of flights coincide in B mode with those of the selected sub-region in A mode are only considered.

For the isolation, the sum of amplitudes of the acoustic signals determined at each point P may thus be expressed according to $$I^B(P) = \sum_{i=1}^{M} \sum_{j=1}^{N} A_{ij}^B(P),$$

where the amplitude $A_{ij}^B(P)$ is given by $$A_{ij}^B(P) = \begin{cases} S_{ij}(T_{ij}^B(P)) & \text{if } T_{ij}^B(P) \in T_{ij}^A(\tilde{Z}) \\ 0 & \text{otherwise} \end{cases}$$

To carry out the filtering of reconstruction artefacts in the second image, one determines, for each point P of the region Z, a sum of amplitudes of the acoustic signals only taking account of the acoustic signals received at a receiver j from a transmitter i when the time of flight $T_{ij}^B(P)$ of the path according to the second reconstruction mode from the transmitter i to the receiver j while going through the point P does not coincide with the times of flight of the paths according to the first reconstruction mode from the transmitter i to the receiver j while going through the points of the selected sub-region $(T_{ij}^B(P) \notin T_{ij}^A(\tilde{Z}))$.

Thus, during the reconstruction according to the B mode, the contributions $S_{ij}(T_{ij}^B(P))$ of the points for which the times of flights coincide in B mode with those of the selected sub-region in A mode are not considered.

For the filtering, the sum of amplitudes of the acoustic signals determined at each point P may thus be expressed according to $$I^B(P) = \sum_{i=1}^{M} \sum_{j=1}^{N} A_{ij}^B(P),$$

where the amplitude $A_{ij}^B(P)$ is given by $$A_{ij}^B(P) = \begin{cases} 0 & \text{if } T_{ij}^B(P) \in T_{ij}^A(\tilde{Z}) \\ S_{ij}(T_{ij}^B(P)) & \text{otherwise} \end{cases}$$

Figure 5:
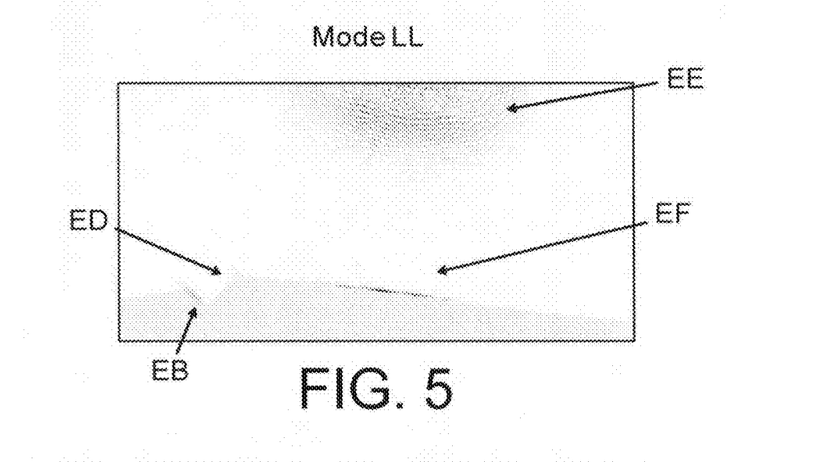
FIG. 5 illustrates different indications present in the image of a part reconstructed by a first reconstruction mode of direct LL type.

Given the celerity difference existing between the waves L and T, the analysis of the images is preferentially carried out by considering firstly the fastest modes of propagation (direct LL for example) then the slowest (direct LT and corner echo LLL for example). In fact, in the case of the direct LL mode, the risks of presence of reconstruction artefacts stemming from a slower mode of propagation are reduced. In particular, for the sub-region considered, this mode will not be able to contain any indication linked to a geometry echo detected according to direct LT or corner echo LLL modes, which makes the nature of the observable indications more easily interpretable. FIG. 5 gives in this respect an example of image reconstructed according to the direct LL mode in which may be observed the presence of an echo from the bottom of the part EF right in front of the transducer, of a geometry echo EB linked to the welding bead, of indications linked to the echo EE of emission and an echo ED linked to the emerging cut.

The previously described method may be applied to these different indications in order to predict the artefacts that will be associated therewith in other reconstruction modes.

Figure 6C:
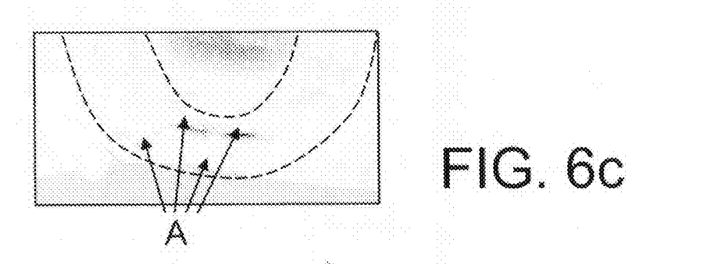
FIG. 6c is a further illustration of the application of a method according to the invention with a first reconstruction mode of direct LL type and a second reconstruction mode of direct LT type.

FIGS. 6a-6c give an example of implementation of the method during an isolation of artefacts in a reconstruction according to the direct LT mode. FIG. 6a is an image reconstructed according to the LL mode (A mode) in which echoes may be observed in the selected sub-region Ž. These echoes induce artefacts in an image reconstructed according to the LT mode (B mode) in the area surrounded by dotted lines in FIG. 6b which comprises the points for which the time of flight of the path in LT mode correspond to a time of flight of the path in LL mode going through a point of the selected sub-region $\tilde{Z}$ (transformation in B mode of the sub-region $\tilde{Z}$). FIG. 6c illustrates a reconstruction in standard LT mode. Comparison of FIGS. 6b and 6c then makes it possible to interpret the nature of a large number of indications, in particular the presence of artefacts A.

Figure 7A:
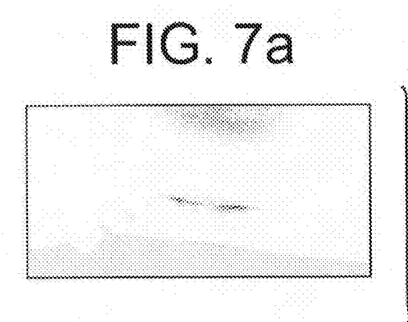
FIG. 7a illustrates the filtering of artefacts in a reconstruction according to a mode of direct LT type.
Figure 7B:
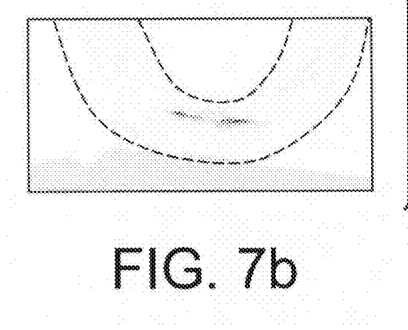
FIG. 7b is another illustration of the filtering of artefacts in a reconstruction according to a mode of direct LT type.
Figure 7C:
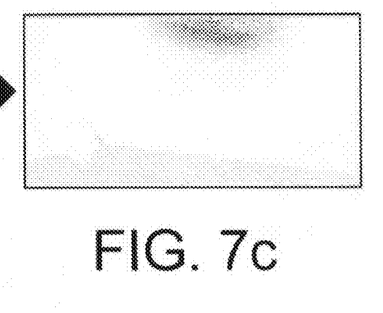
FIG. 7c is a further illustration of the filtering of artefacts in a reconstruction according to a mode of direct LT type.

FIGS. 7a-7c illustrate for their part an example of implementation of the method during a filtering of artefacts in a reconstruction according to the LT mode. FIG. 7a corresponds to FIG. 6c and illustrates a reconstruction in standard LT mode. FIG. 7b corresponds to FIG. 6b and illustrates a transformation in B mode of the selected sub-region $\tilde{Z}$. FIG. 7c illustrates for its part the result of the filtering according to the invention, where the second image of the region is cleared of the artefacts A of FIG. 6c induced by the echoes observed in the sub-region $\tilde{Z}$ of the first image.

Figure 8A:
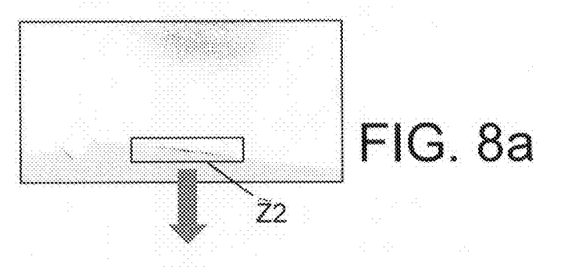
FIG. 8a is a first illustration of the application of a method according to the invention with a first reconstruction mode of direct LL type and a second reconstruction of corner echo LLL mode type, with selection of two different regions in an image reconstructed while considering a first reconstruction mode of direct LL type.
Figure 8B:
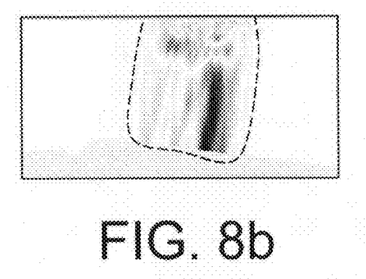
FIG. 8b is a second illustration of the application of a method according to the invention with a first reconstruction mode of direct LL type and a second reconstruction of corner echo LLL mode type, with selection of two different regions in an image reconstructed while considering a first reconstruction mode of direct LL type.
Figure 8C:
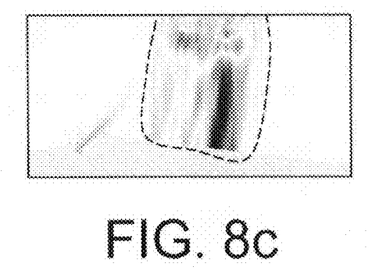
FIG. 8c is a third illustration of the application of a method according to the invention with a first reconstruction mode of direct LL type and a second reconstruction of corner echo LLL mode type, with selection of two different regions in an image reconstructed while considering a first reconstruction mode of direct LL type.
Figure 9A:
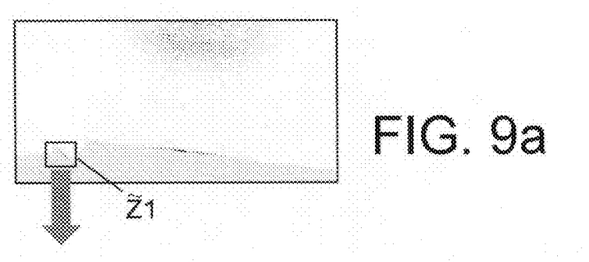
FIG. 9a is a fourth illustration of the application of a method according to the invention with a first reconstruction mode of direct LL type and a second reconstruction of corner echo LLL mode type, with selection of two different regions in an image reconstructed while considering a first reconstruction mode of direct LL type.
Figure 9B:
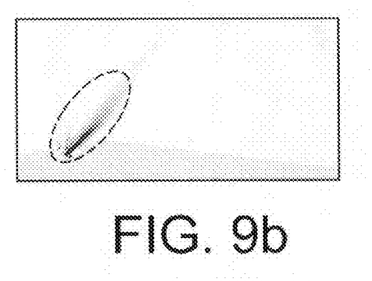
FIG. 9b is a fifth illustration of the application of a method according to the invention with a first reconstruction mode of direct LL type and a second reconstruction of corner echo LLL mode type, with selection of two different regions in an image reconstructed while considering a first reconstruction mode of direct LL type.
Figure 9C:
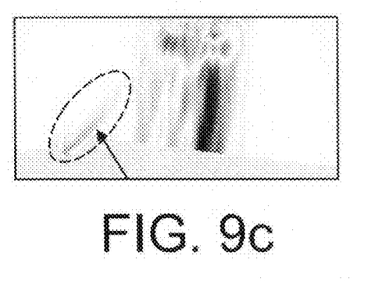
FIG. 9c is a sixth illustration of the application of a method according to the invention with a first reconstruction mode of direct LL type and a second reconstruction of corner echo LLL mode type, with selection of two different regions in an image reconstructed while considering a first reconstruction mode of direct LL type.

FIGS. 8a-8c, respectively 9a-9c, give an example of implementation of the method during an isolation of artefacts in a reconstruction according to the corner echo LLL mode. FIG. 8a, respectively 9a, is an image reconstructed according to the direct LL mode (A mode) in which echoes are observable in a selected sub-region $\tilde{Z}$ 1, respectively $\tilde{Z}$ 2. These echoes induce artefacts in an image reconstructed according to the LLL mode (B mode) in the area surrounded by dotted lines in FIG. 8b, respectively 9b, which corresponds to the transformation in B mode of the sub-region $\tilde{Z}$. FIG. 8c, respectively 9c, illustrates a reconstruction in standard LLL mode. Comparison of FIGS. 8b and 8c, respectively 9b and 9c, then makes it possible to interpret the nature of a large number of indications, in particular the presence of artefacts.

Figure 10A:
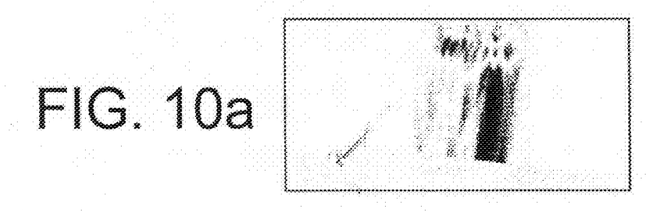
FIG. 10a is a first illustration of the filtering of artefacts in a reconstruction according to a mode of corner echo LLL type.
Figure 10B:
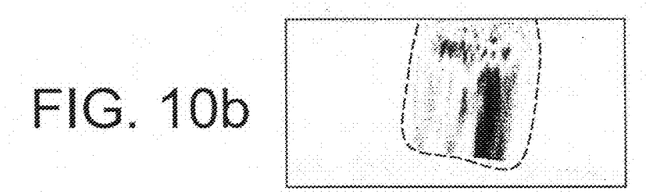
FIG. 10b is a second illustration of the filtering of artefacts in a reconstruction according to a mode of corner echo LLL type.
Figure 10C:
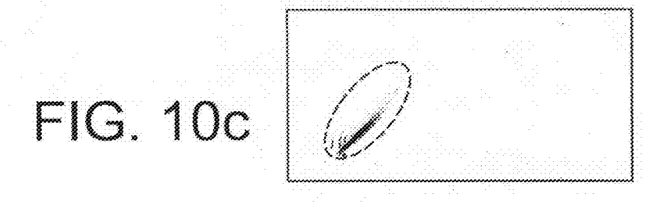
FIG. 10c is a third illustration of the filtering of artefacts in a reconstruction according to a mode of corner echo LLL type.
Figure 10D:
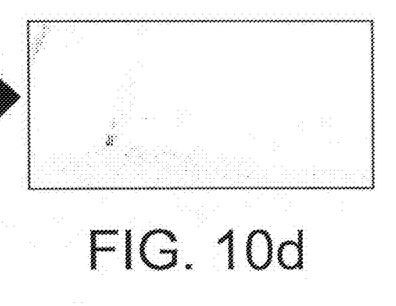
FIG. 10d is a fourth illustration of the filtering of artefacts in a reconstruction according to a mode of corner echo LLL type.

FIGS. 10a-10d illustrate for their part an example of implementation of the method during a filtering of artefacts in a reconstruction according to the LLL mode. FIG. 10a corresponds to FIGS. 8c and 9c and illustrates a reconstruction in standard LLL mode. FIG. 10b corresponds to FIG. 8b and illustrates transformation in B mode of the sub-region $\tilde{Z}$ 2. FIG. 10c corresponds to FIG. 9b and illustrates the transformation in B mode of the sub-region $\tilde{Z}$ 1. FIG. 10d illustrates for its part the result of the filtering according to the invention, where the second image of the region is cleared of the artefacts induced by the echoes observed in the sub-regions $\tilde{Z}$ 1 and $\tilde{Z}$ 2 of the first image.

The invention is not limited to the previously described method, but also extends to an ultrasound imaging device for imaging a part 1 capable to implement this method, particularly a device comprising M transmitters of an ultrasound signal in the part to be imaged 1 and N receivers of an ultrasound signal $S_{ij}(t)$ coming from the part to be imaged, the index i designating one of the transmitters, the index j designating one of the receivers, and t representing the time, and a processor coupled to the M transmitters and the N receivers, the processor being configured to:
    select a first sub-region of the part from a first image of a region of the part 1,
    determine, for each point P of the first selected sub-region, times of flight of the paths according to a first reconstruction mode going through the point P from a transmitter i to a receiver j for a set of M*N transmitter-receiver couples of an ultrasound signal;
    determine a second sub-region of the part, a point P* of the region belonging to the second sub-region when a time of flight of the path according to a second reconstruction mode going through the point P* from a transmitter i to a receiver j of said set of M*N transmitter-receiver couples coincides with a time of flight of a path according to the first reconstruction mode from the transmitter i to the receiver j going through one of the points of the first selected sub-region.

And the invention also extends to a computer program product comprising code instructions for the execution of the steps of the previously described method, when said program is run on a computer.

It will have been understood from the present description that the invention makes it possible to analyse the origin of indications present in reconstructions by multimodal synthetic focusing and thus to distinguish echoes due to defects from those due to the geometry of the part. The invention has moreover the advantage of applying to all multimodal reconstructions. It moreover uses the same parameters as standard synthetic focusing, and thus does not require additional calculations or measurements. It can in addition be used not only for an identification of artefacts, but also for filtering of the latter.

The invention claimed is:

1. A method of inspecting a structure to detect a presence of potential defects therein, including steps implemented by a processor coupled to a multi element transducer having M transmitters of an ultrasound signal and N receivers of the ultrasound signal, the method comprising:
    transmitting successively via the M transmitters the ultrasound signal in the structure, and recording in the N receivers echoes combining from propagation of the ultrasound signal in the structure, to acquire a set of M*N ultrasound signals $S_{ij}(t)$, where i denotes one of the transmitters, j denotes one of the receivers, and t denotes time;
    determining, for each point of a first sub-region of a region of the structure and for each transmitter-receiver pair i-j, a time of flight of a path in accordance with a first ultrasound wave propagation model that goes through the point from a corresponding transmitter i to a corresponding receiver j;
    determining a second sub-region of the region of the structure, wherein for each transmitter-receiver pair i-j a point of the region belongs to the second sub-region when a time of flight of a path in accordance with a second ultrasound wave propagation model that goes through the point from the corresponding transmitter i to the corresponding receiver j coincides with a time of flight of a path in accordance with the first ultrasound wave propagation model that goes through one of the points of the first sub-region from the corresponding transmitter i to the corresponding receiver j;
    forming an image of the region of the structure by synthetic focusing, wherein for each point of the region, and for each transmitter-receiver pair i-j, an ultrasound signal considered at a time of flight of the path in accordance with the second ultrasound wave propagation model that goes through the point of the region from the corresponding transmitter i to the corresponding receiver j is exploited uniquely if said time of flight coincides with one, or differs with all, of the times of flight of the paths in accordance with the first ultrasound wave propagation model that goes through one of the points of the first sub-region from the corresponding transmitter i to the corresponding receiver j.

2. The method of claim 1, wherein forming the image comprises, for each point of the region, determination of a sum of amplitudes of acoustic signals limited to the acoustic signals received at the corresponding receiver j from the corresponding transmitter i when the time of flight of the path in accordance with the second ultrasound wave propagation model that goes through the point from the corresponding transmitter i to the corresponding receiver j coincides with a time of flight of a path in according with the first ultrasound wave propagation model that goes through one of the points of the first sub-region from the corresponding transmitter i to the corresponding receiver j.

3. The method of claim 1, wherein forming the image comprises, for each point of the region, determination of a sum of amplitudes of acoustic signals limited to acoustic signals received at the corresponding receiver j from the corresponding transmitter i when the time of flight of the path in accordance with the second ultrasound wave propagation model that goes through the point from the corresponding transmitter i to the corresponding receiver j does not coincide with one of the times of flight of the paths in accordance with the first ultrasound wave propagation model that goes through the points of the first sub-region from the corresponding transmitter i to the corresponding receiver j.

4. The method of claim 1, wherein each one of the first and second ultrasound wave propagation models includes a type of route comprising several portions and a mode of propagation of the ultrasound signal on each portion of the route.

5. The method of claim 4, wherein the first ultrasound wave propagation model is a model according to which each ultrasound signal follows a direct route with two portions, a mode of propagation of the ultrasound signal being lateral on each of the portions.

6. The method of claim 5, wherein the second ultrasound wave propagation model is a model according to which each ultrasound signal follows a direct route with two portions and a mode of propagation of the signal is different on each of the portions, or a model according to which each ultrasound signal follows an indirect route with three portions at least.

7. A non-transitory computer-readable medium storing computer-readable instructions thereon that, when executed by a computer, cause the computer to perform the method according to claim 1.

8. An inspecting device for detecting potential defects in a structure, comprising:

M transmitters of an ultrasound signal in the structure to be image;

N receivers of an ultrasound signal $S_{ij}(t)$ coming from the structure to be imaged, the index i designating one of the transmitters, the index j designating one of the receivers, and t representing time; and a processor coupled to the M transmitters and the N receivers, wherein the processor is configured to:

determine, for each point of a first sub-region of a region of the structure, and for each transmitter-receiver pair i-j, a time of flight corresponding to a path in accordance with a first ultrasound wave propagation model that goes through the point from a corresponding transmitter i to a corresponding receiver j;

determine a second sub-region of the region of the structure, wherein for each transmitter-receiver pair i-j a point of the region belongs to the second sub-region when a time of flight of a path in accordance with a second ultrasound wave propagation model that goes through the point from the corresponding transmitter i to the corresponding receiver j coincides with a time of flight of a path in accordance with the first ultrasound wave propagation model that goes through one of the points of the first sub-region from the corresponding transmitter i to the corresponding receiver j;

forming an image of the region of the structure by synthetic focusing, wherein for each point of the region, and for each transmitter-receiver pair i-j, an ultrasound signal considered at the time of flight of the path in accordance with the second ultrasound wave propagation model that goes through the point of the region from the corresponding transmitter i to the corresponding receiver j is exploited uniquely if said time of flight coincides with one, or differs with all, of the times of flight of the paths in accordance with the first ultrasound wave propagation model that goes through one of the points of the first sub-region from the corresponding transmitter i to the corresponding receiver j.

* * * * *